(12) United States Patent
Ma et al.

(10) Patent No.: US 12,023,159 B2
(45) Date of Patent: Jul. 2, 2024

(54) BLOOD DRAW SYRINGE WITH HEMOLYSIS PROTECTION

(71) Applicant: Becton, Dickinson and Company, Franklin Lakes, NJ (US)

(72) Inventors: Yiping Ma, Layton, UT (US); Jordan Ciciliano, Durham, NC (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 371 days.

(21) Appl. No.: 17/496,858

(22) Filed: Oct. 8, 2021

(65) Prior Publication Data

US 2022/0110562 A1  Apr. 14, 2022

Related U.S. Application Data

(60) Provisional application No. 63/090,602, filed on Oct. 12, 2020.

(51) Int. Cl.
*A61B 5/15* (2006.01)
(52) U.S. Cl.
CPC .. *A61B 5/150992* (2013.01); *A61B 5/150236* (2013.01)
(58) Field of Classification Search
None
See application file for complete search history.

(56) References Cited

U.S. PATENT DOCUMENTS

| | | | |
|---|---|---|---|
| 4,492,634 A | 1/1985 | Villa-Real | |
| 4,894,052 A | 1/1990 | Crawford | |
| 5,156,596 A | 10/1992 | Balbierz et al. | |
| 5,873,841 A | 2/1999 | Brannon | |
| 7,713,256 B2 | 5/2010 | Brimhall et al. | |
| 8,690,833 B2 | 4/2014 | Belson | |
| 9,658,628 B2 * | 5/2017 | Burt | F24F 11/84 |
| 2003/0055381 A1 | 3/2003 | Wilkinson | |
| 2003/0135237 A1 | 7/2003 | Cragg et al. | |
| 2006/0161115 A1 | 7/2006 | Fangrow | |
| 2008/0312576 A1 | 12/2008 | McKinnon et al. | |
| 2009/0259201 A1 | 10/2009 | Hwang et al. | |
| 2011/0009717 A1 | 1/2011 | Davis et al. | |
| 2014/0042094 A1 | 2/2014 | Montagu et al. | |
| 2015/0025348 A1 | 1/2015 | Grabowski | |
| 2016/0324455 A1 | 11/2016 | Crosby et al. | |
| 2018/0140240 A1 | 5/2018 | Bullington et al. | |

(Continued)

FOREIGN PATENT DOCUMENTS

CN  110141255 A  8/2019
EP  1293162 A2  3/2003

(Continued)

*Primary Examiner* — Yi-Shan Yang
(74) *Attorney, Agent, or Firm* — The Webb Law Firm (57) ABSTRACT

A blood collection device may include a syringe with hemolysis protection. The syringe with hemolysis protection may be coupled to a catheter assembly and used for blood draw. The blood collection device may include the syringe, which may include a distal end, and a flow restrictor. The flow restrictor may include a distal end and a proximal end. The proximal end of the flow restrictor may be coupled to the distal end of the syringe, which may protect against hemolysis.

19 Claims, 5 Drawing Sheets

(56) References Cited

U.S. PATENT DOCUMENTS

| | | | |
|---|---|---|---|
| 2019/0021640 A1 | 1/2019 | Burkholz et al. | |
| 2019/0076074 A1* | 3/2019 | Bullington | ......... A61B 5/15003 |
| 2019/0236956 A1 | 8/2019 | Uchimura et al. | |
| 2019/0321599 A1 | 10/2019 | Burkholz et al. | |
| 2019/0374144 A1 | 12/2019 | Langdell et al. | |
| 2020/0170559 A1 | 6/2020 | Burkholz et al. | |
| 2021/0228127 A1 | 7/2021 | Burkholz et al. | |

FOREIGN PATENT DOCUMENTS

| | | |
|---|---|---|
| EP | 3207970 A1 | 8/2017 |
| WO | 9213584 A1 | 8/1992 |
| WO | 9834532 A1 | 8/1998 |
| WO | 2004032995 A2 | 4/2004 |
| WO | 2013028759 A1 | 2/2013 |
| WO | 2019236956 A2 | 12/2019 |

* cited by examiner

BLOOD DRAW SYRINGE WITH HEMOLYSIS PROTECTION

CROSS-REFERENCE TO RELATED APPLICATION

The present application claims priority to U.S. Provisional Application Ser. No. 63/090,602, entitled "Blood Draw Syringe with Hemolysis Protection", filed Oct. 12, 2020, the entire disclosure of which is hereby incorporated by reference in its entirety.

BACKGROUND

A catheter is commonly used to infuse fluids into vasculature of a patient. For example, the catheter may be used for infusing normal saline solution, various medicaments, or total parenteral nutrition.

The catheter may include a peripheral intravenous ("IV") catheter. In this case, the catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may remove the introducer needle, leaving the catheter in place for future fluid infusion.

Blood draws through peripheral intravenous catheters are not routinely performed, in large part due to a risk of hemolysis of a blood sample withdrawn through the peripheral intravenous catheter. When blood draw is performed through the peripheral intravenous catheter, a commonly used blood collection container is a VACUTAINER® blood collection tube, available from Becton Dickinson & Company. In some instances, a syringe may instead be used. However, the syringe has not been shown to reduce a risk of hemolysis compared to the VACUTAINER®.

Unfortunately, as blood is drawn into the syringe or VACUTAINER®, red blood cells are in a high shear stress state and susceptible to hemolysis due to a high pressure differential between the vein and the syringe or VACUTAINER®. Hemolysis may result in rejection and discard of a blood sample. The high pressure differential can also result in catheter tip collapse, vein collapse, or other complications.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to a blood collection device and related devices, systems, and methods. In some embodiments, a blood collection system may include a catheter assembly, which may include a catheter adapter and a catheter extending distally from the catheter adapter. In some embodiments, the blood collection system may include the blood collection device coupled to the catheter assembly. In some embodiments, the blood collection device may include a syringe, which may include a distal end. In some embodiments, the blood collection device may include a flow restrictor, which may include a distal end and a proximal end. In some embodiments, the proximal end of the flow restrictor may be coupled to the distal end of the syringe.

In some embodiments, the catheter assembly may include an extension tube. In some embodiments, a distal end of the extension tube may be integrated with the catheter adapter. In some embodiments, the blood collection device may be coupled to a proximal end of the extension tube.

In some embodiments, the distal end of the syringe may include a first luer adapter. In some embodiments, the proximal end of the flow restrictor may include a second luer adapter coupled to the first luer adapter. In some embodiments, the flow restrictor may be monolithically formed as a single unit. In these and other embodiments, the distal end of the flow restrictor may include a third luer adapter.

In some embodiments, the distal end of the flow restrictor may include the third luer adapter. In these and other embodiments, the flow restrictor may include an extension tube disposed between the second luer adapter and the third luer adapter. In these and other embodiments, the flow restrictor may include a first piece monolithically formed as a single unit and a second piece monolithically formed as a single unit. In some embodiments, a proximal end of the extension tube may be integrated within the first piece. In some embodiments, a distal end of the extension tube may be integrated within the second piece. In some embodiments, the first piece may include the second luer adapter. In some embodiments, the second piece may include the third luer adapter.

In some embodiments, a geometric factor of the flow restrictor is represented by $G_f$. In some embodiments, $G_f$ may be $1.43E7$ $1/in^3 \pm 30\%$. In some embodiments, $G_f$ may be $3.70E6$ $1/in^3 \pm 30\%$. In some embodiments, $G_f$ may be between $1.43E7$ and $3.70E6$. In some embodiments, $G_f$ may be $1.43E7$ $1/in^3 \pm 10\%$ or $3.70E6$ $1/in^3 \pm 10\%$.

In some embodiments, the flow restrictor may include a fluid pathway extending through the flow restrictor. In some embodiments, a diameter of the fluid pathway may be uniform along an entirety of a length of the fluid pathway. In these embodiments, the diameter is represented by D, the length is represented by L, and $D^4/L$ may be $2.7E-7$ or $7.0E-8$.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE DRAWINGS

Example embodiments will be described and explained with additional specificity and detail through the use of the accompanying drawings in which.

DESCRIPTION OF EMBODIMENTS

Figure 1A:
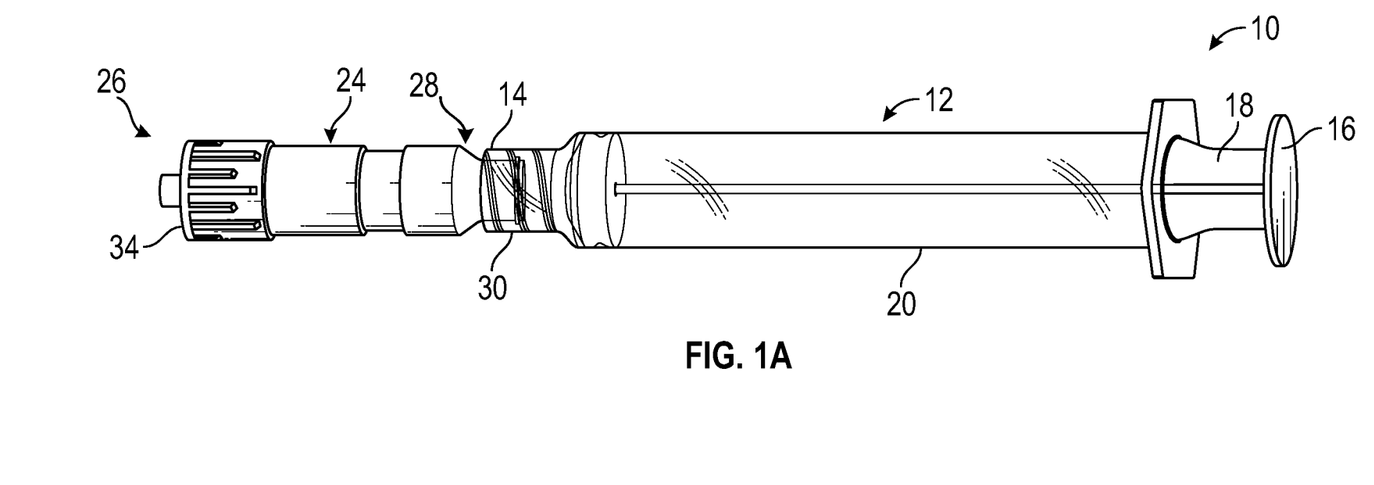
FIG. 1A is an upper perspective view of an example blood collection device that includes hemolysis protection, according to some embodiments.
Figure 1B:
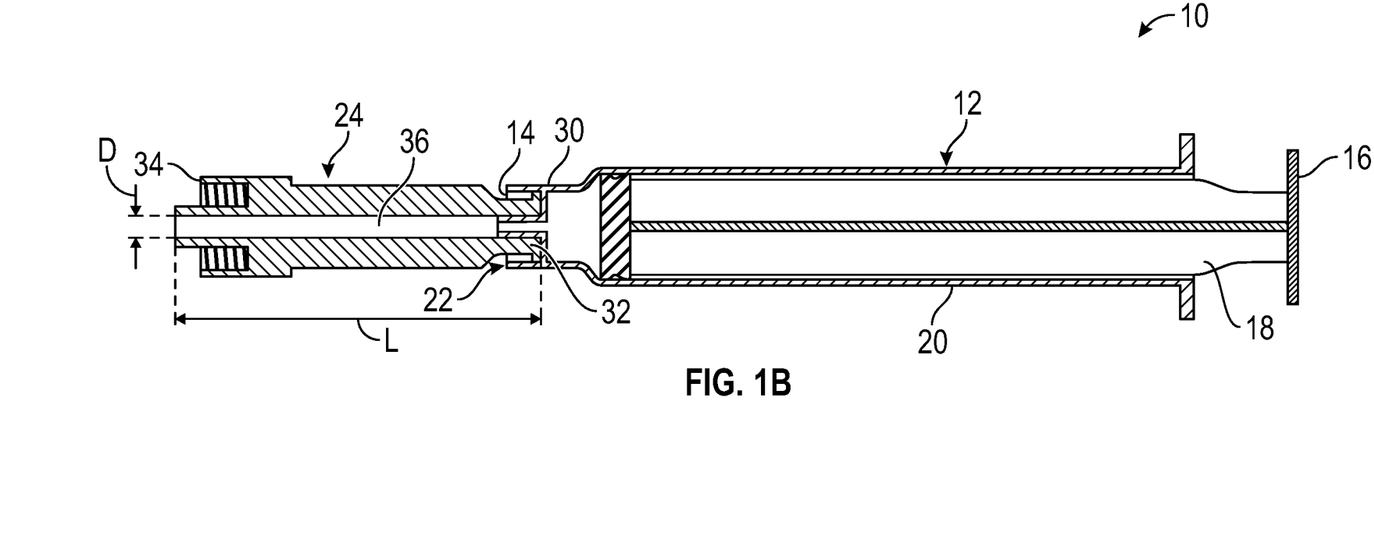
FIG. 1B is a cross-sectional view of the blood collection device of FIG. 1A, according to some embodiments.

In some embodiments, a blood collection device 10 may include a syringe 12, which may include a distal end 14 and a proximal end 16. In some embodiments, the syringe 12 may include a sliding plunger 18 that fits tightly in a barrel or tube 20. In some embodiments, the sliding plunger 18 may be pulled proximally with respect to the tube 20, allowing the syringe 12 to draw in a liquid, such as blood, through an orifice 22 at the distal end 14. In some embodiments, the sliding plunger 18 may be pushed distally with respect to the tube 20, allowing the syringe 12 to then expel the liquid through the orifice 22. In some embodiments, the syringe 12 may be configured to hold between about 1 and 20 milliliters of the liquid.

In some embodiments, the blood collection device 10 may include a flow restrictor 24, which may include a distal end 26 and a proximal end 28. In some embodiments, the proximal end 28 of the flow restrictor 24 may be coupled to the distal end 14 of the syringe 12. In some embodiments, the flow restrictor 24 may be removably coupled to the distal end 14 of the syringe 12. In other embodiments, the flow restrictor 24 may be permanently coupled to the distal end 14 of the syringe 12.

In some embodiments, the distal end 14 of the syringe 12 may include a first luer adapter 30. In some embodiments, the proximal end 16 of the flow restrictor 24 may include a second luer adapter 32 coupled to the first luer adapter 30. In some embodiments, the first luer adapter 30 may include a male luer adapter, which may be threaded or engaged in a slip-fit with the second luer adapter 32, which may include a female luer adapter. In some embodiments, a threaded connection between the first luer adapter 30 and the second luer adapter 32 may prevent accidental uncoupling of the syringe 12 from the flow restrictor 24 during blood collection.

In some embodiments, the flow restrictor 24 may be monolithically formed as a single unit, as illustrated, for example, in FIGS. 1A-1B. In these and other embodiments, the distal end 26 of the flow restrictor 24 may include a third luer adapter 34. In some embodiments, the third luer adapter 34 may include a male luer adapter. In some embodiments, the distal end 26 of the flow restrictor 24 may be configured to couple to a catheter assembly, which may be inserted into vasculature of a patient. In some embodiments, the sliding plunger 18 may be pulled in a proximal direction to withdraw blood from vasculature of the patient into the tube 20 of the syringe 12.

In some embodiments, a length of the flow restrictor 24 may be less than a length of the syringe 12 to facilitate easy handling by a user. In some embodiments, the flow restrictor 24 may include a fluid pathway 36 extending through the flow restrictor 24. Generally, blood cells experience shear stress as blood flows in a fluid pathway. The maximum shear stress is along the wall of the blood cell, or wall shear stress. Wall shear stress on blood cells is considered a major source of hemolysis and mechanical damage to blood cells.

In some embodiments, the flow restrictor 24 may provide hemolysis protection. In further detail, the flow restrictor 24 may limit a maximum blood collection rate, which in turn may limit a maximum shear stress during blood collection and reduce hemolysis. In some embodiments, the flow restrictor 24 may be configured to limit a maximum shear stress that blood cells are exposed to during a syringe draw to a predetermined or target value.

Fluid flow in a flow restrictor with a tubular fluid pathway therethrough can be analyzed using Poiseuille's equation:

$$Q = \frac{\pi D^4 \Delta P}{128 \mu L} = \frac{\Delta P}{R_f}$$

where P is a change in pressure gradient across the flow restrictor, D and L are the inner diameter and length, respectively, of the fluid pathway 36 through the flow restrictor, $\mu$ is the viscosity of a fluid, and $$R_f = \frac{128 \mu L}{\pi D^4}$$

is the fluid resistance. Since $\mu$ is the viscosity of the fluid and not part of the flow restrictor geometry, a geometric factor $G_f$ is defined such that $R_f$ (the fluid resistance) is $$R_f = \frac{128 \mu}{\pi} G_f,$$

where $$G_f = \frac{L}{D^4}.$$

Figure 2A:
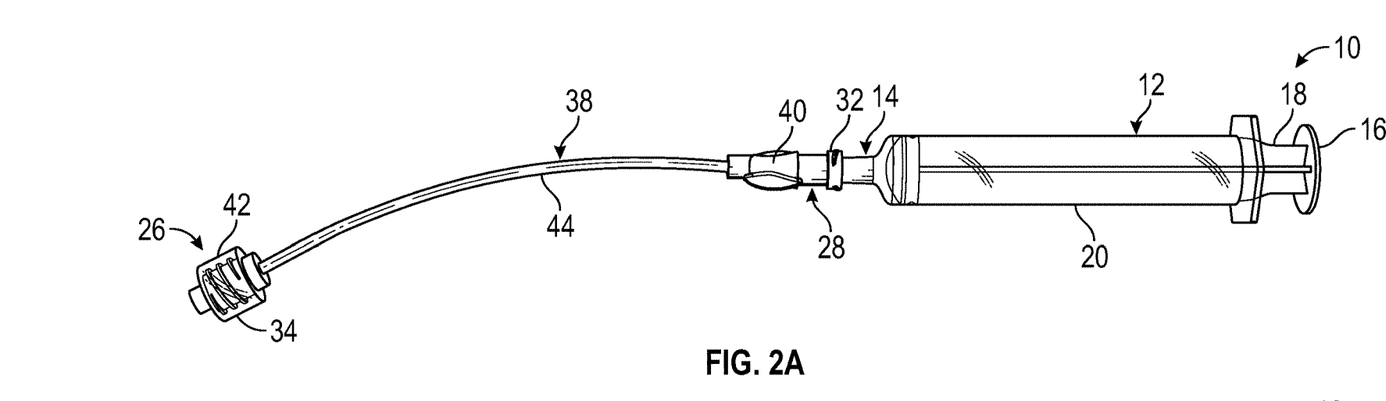
FIG. 2A is an upper perspective view of another example blood collection device that includes hemolysis protection, according to some embodiments.
Figure 2B:
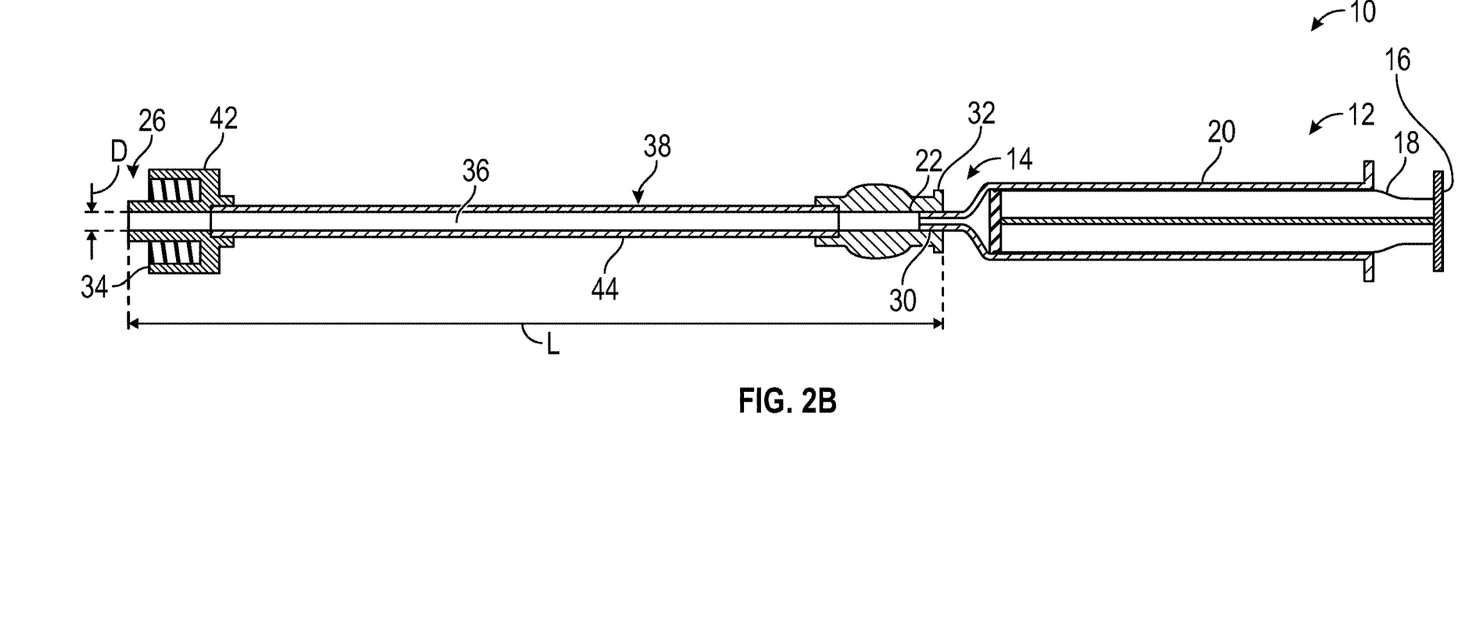
FIG. 2B is a cross-sectional view of the blood collection device of FIG. 2A, according to some embodiments.

In some embodiments, the flow restrictor may include the flow restrictor 24 or the flow restrictor 38 (see, for example, FIGS. 2A-2B).

In response to the fluid pathway 36 having multiple sections with lengths (L1, L2, L3) and inner diameters of (D1, D2, D3), the fluid resistance is:

$$G_f = \frac{L1}{D1^4} + \frac{L2}{D2^4} + \frac{L3}{D3^4}$$

In some embodiments, the flow restrictor may be configured to limit $G_f$, and thereby limit hemolysis. For example, for the flow restrictor 24, $G_f$ may be about 1.43E7 l/in³. In some embodiments, for the flow restrictor 24, $G_f$ may be 1.43E7 l/in³±10% or 1.43E7 l/in³±30%.

In some embodiments, an inner diameter of the fluid pathway 36 may be uniform along an entirety of a length of the fluid pathway 36. In some embodiments, $D^4/L$ is about 2.7E-7 which may reduce the wall sheer stress to reduce hemolysis when the flow restrictor 24 is used with a 20 G catheter. In some embodiments, $D^4/L$ is about 7.0E-8, which may reduce the wall sheer stress to reduce hemolysis when the flow restrictor 24 is used with a 22 G catheter.

Referring now to FIGS. 2A-2B, in some embodiments, the blood collection device 10 may include a flow restrictor 38. In some embodiments, the flow restrictor 38 may be similar or identical to the flow restrictor 24 in terms of one or more features and/or operation. In some embodiments, the flow restrictor 38 may also be configured to limit $G_f$, and thereby limit hemolysis. For example, for the flow restrictor 38, $G_f$ may be about 3.70E6 l/in³. In some embodiments, for the flow restrictor 38, $G_f$ may be 3.70E6 l/in³±10% or 3.70E6 l/in³±30%. In some embodiments, a particular flow restrictor, such as, for example, the flow restrictor 24 or the flow restrictor 38, may have a $G_f$ between 1.43E7 and 3.70E6. In some embodiments, the inner diameter of the fluid pathway 36 may be variable along a length of the fluid pathway 36. In these and other embodiments, the flow restrictor 38 may include multiple sections formed with tubes having different inner diameters that are joined together or a single tube with a varying inner diameter along its length.

In some embodiments, the distal end 26 of the flow restrictor 38 may include the third luer adapter 34. In these and other embodiments, the flow restrictor 38 may include an extension tube 44 disposed between the second luer adapter 32 and the third luer adapter 34. In these and other embodiments, the flow restrictor 38 may include a first piece 40 monolithically formed as a single unit and/or a second piece 42 monolithically formed as a single unit. In some embodiments, a proximal end of the extension tube 44 may be integrated within the first piece 40. In some embodiments, a distal end of the extension tube 44 may be integrated within the second piece 42. In some embodiments, the first piece 40 may include the second luer adapter 32. In some embodiments, the second piece 42 may include the third luer adapter 34.

In some embodiments, a length of the flow restrictor 38 may be less than the length of the syringe 12 to facilitate easy handling by the user. In some embodiments, the flow restrictor 38 may include the fluid pathway 36 extending through the flow restrictor 24. In some embodiments, the inner diameter of the fluid pathway 36 may be uniform along an entirety of the length of the fluid pathway 36. In some embodiments, the inner diameter is represented by D, the length is represented by L, and $D^4/L$ is 2.7E-7, which may reduce the wall sheer stress to reduce hemolysis when the flow restrictor 38 is used with a 20 G catheter. In some embodiments, the inner diameter is represented by D, the length is represented by L, and $D^4/L$ is 7.0E-8, which may reduce the wall sheer stress to reduce hemolysis when the flow restrictor 38 is used with a 22 G catheter.

Figure 3:
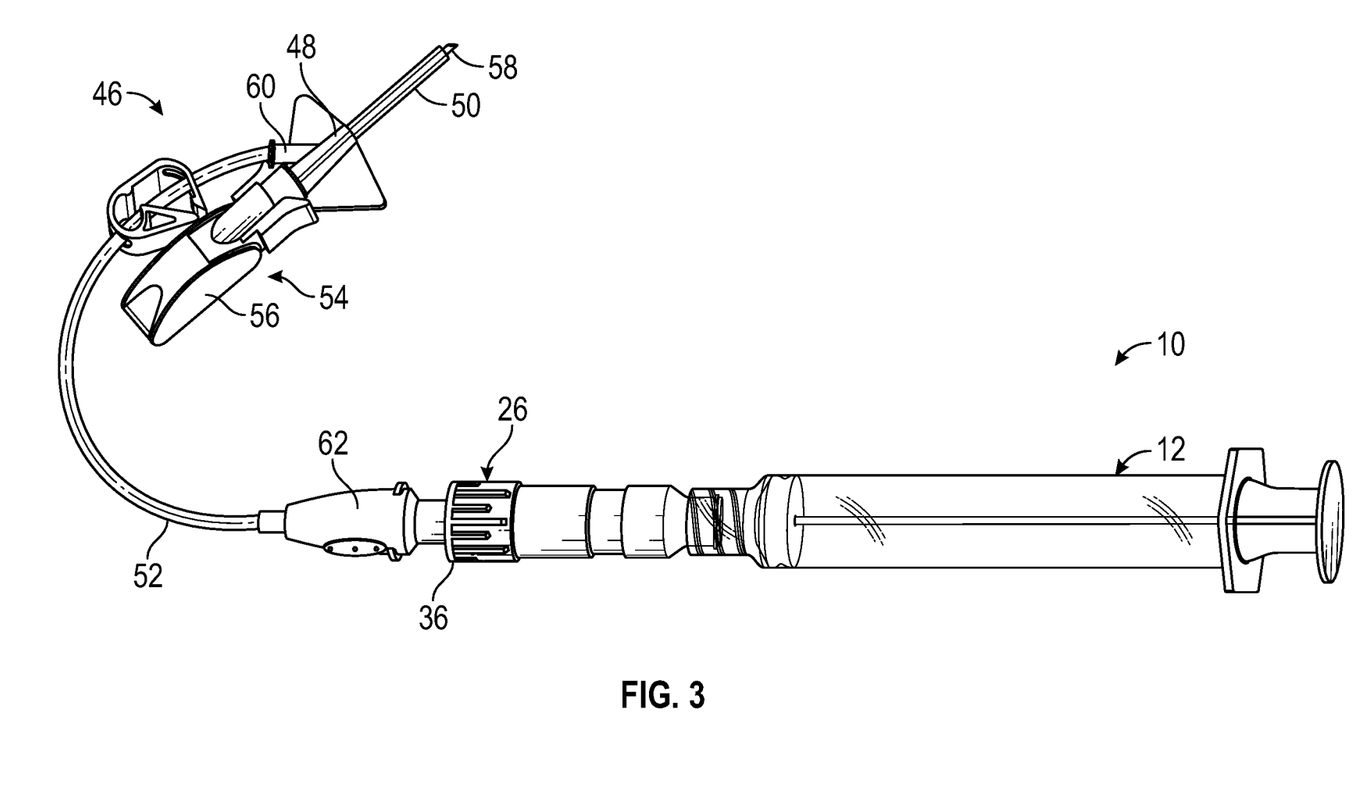
FIG. 3 is an upper perspective view of an example blood collection system, according to some embodiments.

Referring now to FIG. 3, a flow restrictor, such as the flow restrictor 24 (see, for example, FIGS. 1A-1B) or the flow restrictor 38 (see, for example, FIGS. 2A-2B), may be coupled to a catheter assembly 46. In some embodiments, the catheter assembly 46 may include a catheter adapter 48 and a catheter 50 extending distally from the catheter adapter 48. In some embodiments, the catheter assembly 46 may include an extension tube 52. In some embodiments, a distal end of the extension tube 52 may be integrated with the catheter adapter 48. In some embodiments, the blood collection device 10 may be coupled to a proximal end of the extension tube 52.

In some embodiments, a needle assembly 54 may be coupled to the catheter assembly 46. In some embodiments, the needle assembly 54 may include a needle hub 56 and an introducer needle 58 secured within the needle hub 56. In some embodiments, in response to the catheter 50 being inserted into the vasculature of the patient, the needle assembly 54 may be removed from the catheter assembly 46. In some embodiments, the proximal end of the extension tube 52 may be integrated with a side port 60 of the catheter adapter 48.

In some embodiments, the catheter assembly 46 may include or correspond to any suitable catheter assembly, such as, for example, the BD NEXIVA™ Closed IV Catheter system, the BD CATHENA™ Catheter system, the BD VENFLON™ Pro Safely Shielded IV Catheter system, the BD NEOFLON™ IV Cannula system, the BD INSYTE™ AUTOGUARD™ BC Shielded IV Catheter system, or another suitable catheter assembly. In some embodiments, the catheter 50 may include a peripheral intravenous catheter (PIVC), a peripherally inserted central catheter (PICC), a midline catheter, or another suitable catheter.

In some embodiments, in response to insertion of the catheter 50 into the vasculature, blood may flow proximally through a fluid pathway of the catheter assembly 46, which may include one or more of the following: the catheter 50, the catheter adapter 48, the extension tube 52, an adapter 62, the flow restrictor, and the syringe 12.

Figure 4:
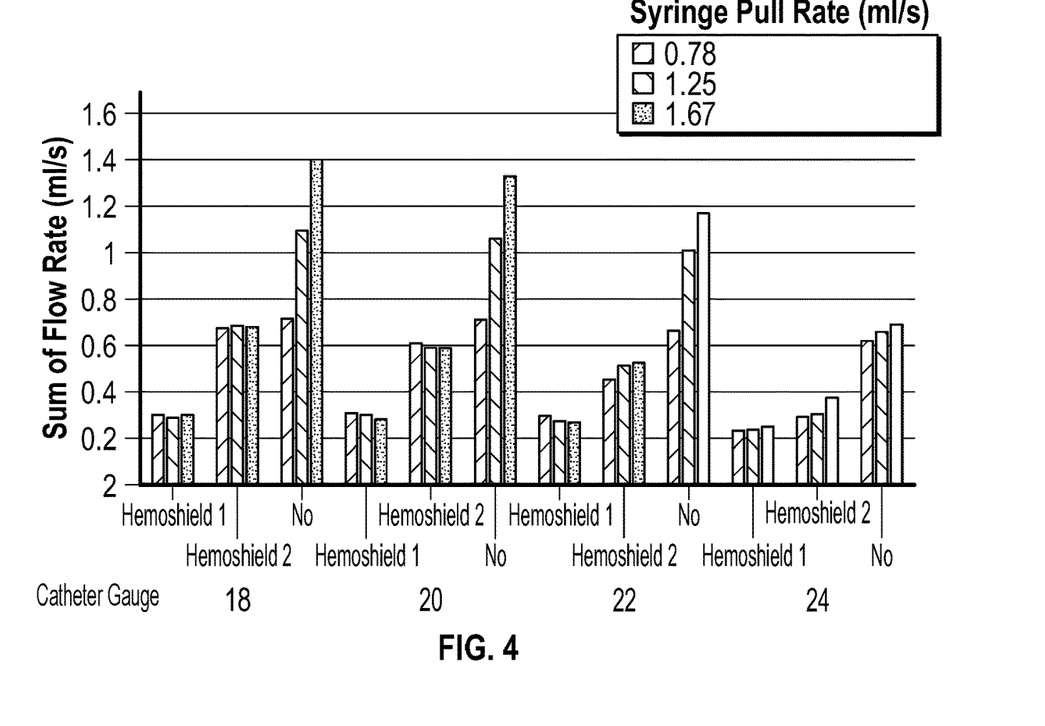
FIG. 4 is a bar graph illustrating blood collection rates with various catheter gauges and flow restrictors under different syringe draw rates, according to some embodiments.

Referring now to FIG. 4, a bar graph illustrates blood collection rates with various catheter gauges and flow restrictors under different syringe draw rates, according to some embodiments. "Hemoshield 1" refers to a first example flow restrictor coupled to a catheter assembly. Hemoshield 1 may include the flow restrictor 24 of FIGS. 1A-1B or the flow restrictor 38 of FIGS. 2A-2B coupled to the catheter assembly. In this example, $D^4/L$ for Hemoshield 1 is about 7 e-8, but $D^4/L$ may vary. "Hemoshield 2" refers to another example flow restrictor coupled to the catheter assembly. Hemoshield 2 may include the flow restrictor 24 of FIGS. 1A-1B of the flow restrictor 38 of FIGS. 2A-2B coupled to the catheter assembly. In this example, $D^4/L$ for Hemoshield 2 is about 2.7 e-8, but $D^4/L$ may vary. "No" refers to the catheter assembly that is not coupled to a flow restrictor.

In the absence of a flow restrictor, the blood flow rate varies significantly with the syringe draw rate. However, with the use of the flow restrictors (Hemoshield 1 and Hemoshield 2 in the experiment), the flow rate through the catheter during blood collection becomes independent of the syringe draw rate. This will greatly reduce variation in syringe draws in the clinical setting, according to some embodiments.

Figure 5:
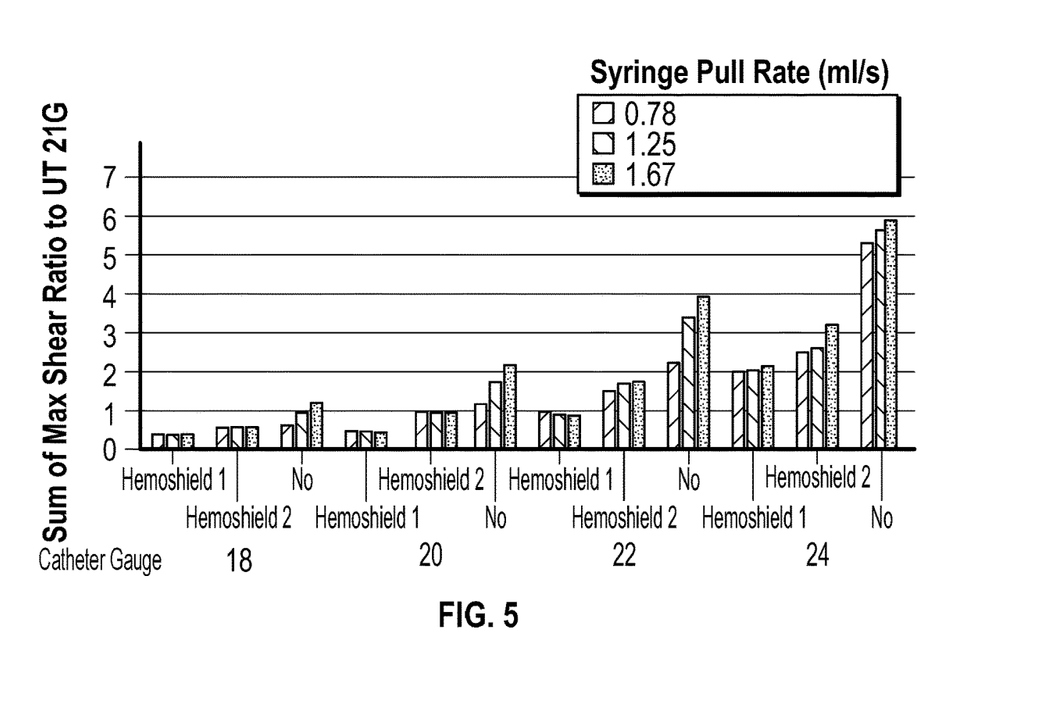
FIG. 5 is a bar graph illustrating maximum shear stress with various catheter gauges and flow restrictors under different syringe draw rates, according to some embodiments.

FIG. 5 is a bar graph illustrating maximum shear stress with various catheter gauges and flow restrictors under different syringe draw rates, according to some embodiments. Again, "Hemoshield 1" refers to the first example flow restrictor coupled to the catheter assembly. Hemoshield 1 may include the flow restrictor 24 of FIGS. 1A-1B or the flow restrictor 38 of FIGS. 2A-2B coupled to the catheter assembly. In this example, $D^4/L$ for Hemoshield 1 is about 7 e-8, but $D^4/L$ may vary. "Hemoshield 2" refers to another example flow restrictor coupled to the catheter assembly. Hemoshield 2 may include the flow restrictor 24 of FIGS.

1A-1B of the flow restrictor 38 of FIGS. 2A-2B coupled to the catheter assembly. In this example, $D^4/L$ for Hemoshield 2 is about 2.7 e-8, but $D^4/L$ may vary. "No" refers to the catheter assembly that is not coupled to a flow restrictor. "UT 21 G" refers to a prior art catheter assembly with a 21 G catheter.

The resultant max shear stress for each catheter gauge can be shown as a ratio to the max shear stress of a UT 21 G with VACUTAINER®, which was previously considered the gold standard for blood draws. As shear stress leads to mechanical hemolysis, reducing the shear stress of catheter draws to that of the UT 21 G reduces the risk of hemolysis. The data shows that for an 18 G catheter, the risk of hemolysis is low when using a syringe to draw blood. However, as the catheter's gauge increases, the risk of hemolysis also increases. For a 20 G catheter, the risk of hemolysis is moderate at low syringe pull rates, but increases at higher pull rates. With a flow restrictor with $D^4/L$ of 2.7 e-7 the max shear with a catheter draw is reduced to the max shear of 21 G UT for all tested syringe draw rates. For a 22 G catheter, the risk of hemolysis is significant at higher draw rates. A flow restrictor with $D^4/L$ of 7 e-8 again reduces the shear rate to that of the gold standard for all tested syringe pull rates. For a 24 G catheter, the tested flow restrictors are able to reduce the max shear stress 2.5 to 3× depending on the syringe draw rate.

Figure 6:
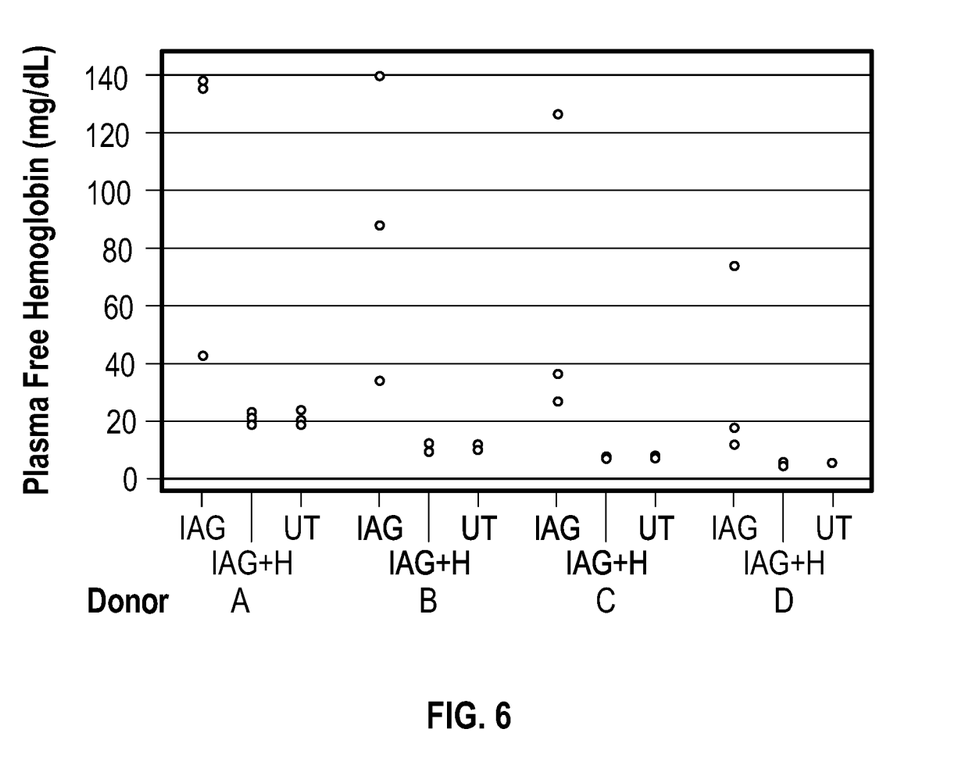
FIG. 6 is a graph illustrating plasma free hemoglobin for catheter assemblies with and without a flow restrictor, according to some embodiments.

FIG. 6 is a graph illustrating plasma free hemoglobin for catheter assemblies with and without a flow restrictor, according to some embodiments. "IAG" refers to a prior art catheter assembly, namely the INSYTE™ AUTO-GUARD™ BC Shielded IV Catheter available from Becton Dickinson & Company of Franklin Lakes, New Jersey "IAG±H" refers to the prior art catheter assembly coupled to a flow restrictor, such as the flow restrictor 24 of FIGS. 1A-1B or the flow restrictor 38 of FIGS. 2A-2B. "UT" refers to another prior art catheter assembly. Hemoshield 1 was used in a hemolysis study with 24 G IAG where all samples were hemolyzed (measured by the presence of plasma free hemoglobin) in the absence of a flow restrictor. With Hemoshield 1, hemolysis was reduced to the level of UT 21 G.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A blood collection device, comprising:
a syringe, comprising a distal end; and
a flow restrictor, comprising a distal end and a proximal end, wherein the proximal end is coupled to the distal end of the syringe, and wherein a geometric factor of the flow restrictor is represented by $G_f$, wherein $G_f$ is at least one of:
(i) 1.43E7 $1/in^3$±30%;
(ii) 3.70E6 $1/in^3$±30%;
(iii) between 1.43E7 $1/in^3$ and 3.70E6 $1/in^3$;
(iv) 1.43E7 $1/in^3$±10%; or
(v) 3.70E6 $1/in^3$±10%.

2. The blood collection device of claim 1, wherein the distal end of the flow restrictor is configured to couple to a catheter assembly.

3. The blood collection device of claim 1, wherein the distal end of the syringe comprises a first luer adapter, wherein the proximal end of the flow restrictor comprises a second luer adapter coupled to the first luer adapter.

4. The blood collection device of claim 3, wherein the flow restrictor is monolithically formed as a single unit.

5. The blood collection device of claim 4, wherein the distal end of the flow restrictor comprises a third luer adapter.

6. The blood collection device of claim 3, wherein the distal end of the flow restrictor comprises a third luer adapter, wherein the flow restrictor further comprises an extension tube disposed between the second luer adapter and the third luer adapter.

7. The blood collection device of claim 6, wherein the flow restrictor comprises a first piece monolithically formed as a single unit and a second piece monolithically formed as a single unit, wherein a proximal end of the extension tube is integrated within the first piece, wherein a distal end of the extension tube is integrated within the second piece, wherein the first piece comprises the second luer adapter, wherein the second piece comprises the third luer adapter.

8. The blood collection device of claim 1, wherein $G_f$ is 1.43E7 $1/in^3$±30%.

9. The blood collection device of claim 1, wherein $G_f$ is 3.70E6 $1/in^3$±30%.

10. A blood collection system, comprising:
a catheter assembly, comprising:
a catheter adapter; and
a catheter extending distally from the catheter adapter; and
the blood collection device of claim 1 coupled to the catheter assembly.

11. The blood collection system of claim 10, wherein the catheter assembly further comprises an extension tube, wherein a distal end of the extension tube is integrated with the catheter adapter, wherein the blood collection device is coupled to a proximal end of the extension tube.

12. The blood collection system of claim 10, wherein the distal end of the syringe comprises a first luer adapter, wherein the proximal end of the flow restrictor comprises a second luer adapter coupled to the first luer adapter.

13. The blood collection system of claim 12, wherein the flow restrictor is monolithically formed as a single unit.

14. The blood collection system of claim 13, wherein the distal end of the flow restrictor comprises a third luer adapter.

15. The blood collection system of claim 12, wherein the distal end of the flow restrictor comprises a third luer adapter, wherein the flow restrictor further comprises an extension tube disposed between the second luer adapter and the third luer adapter.

16. The blood collection system of claim 15, wherein the flow restrictor comprises a first piece monolithically formed as a single unit and a second piece monolithically formed as a single unit, wherein a proximal end of the extension tube is integrated within the first piece, wherein a distal end of the extension tube is integrated within the second piece, wherein the first piece comprises the second luer adapter, wherein the second piece comprises the third luer adapter.

17. The blood collection device system of claim 1, wherein $G_f$ is between 1.43E7 $1/in^3$ and 3.70E6 $1/in^3$.

18. The blood collection device of claim 1, wherein $G_f$ is 1.43E7 $1/in^3$±10%.

19. The blood collection device of claim 1, wherein $G_f$ is $3.70E6$ $1/in^3 \pm 10\%$.

\* \* \* \* \*

UNITED STATES PATENT AND TRADEMARK OFFICE
CERTIFICATE OF CORRECTION

| | | |
|---|---|---|
| PATENT NO. | : 12,023,159 B2 | Page 1 of 1 |
| APPLICATION NO. | : 17/496858 | |
| DATED | : July 2, 2024 | |
| INVENTOR(S) | : Yiping Ma et al. | |

It is certified that error appears in the above-identified patent and that said Letters Patent is hereby corrected as shown below:

In the Claims

Column 8, Line 64, Claim 17, delete "device system" and insert -- device --

Signed and Sealed this
Seventh Day of January, 2025

Derrick Brent
*Acting Director of the United States Patent and Trademark Office*